United States Patent
Horng et al.

(10) Patent No.: US 8,222,899 B2
(45) Date of Patent: Jul. 17, 2012

(54) SQUID DETECTED NUCLEAR MAGNETIC RESONANCE AND IMAGING AT ULTRA-WEAK FIELDS

(76) Inventors: Herng-Er Horng, Taipei County (TW); Hong-Chang Yang, Taipei (TW); Shieh-Yueh Yang, Taipei County (TW)

( * ) Notice: Subject to any disclaimer, the term of this patent is extended or adjusted under 35 U.S.C. 154(b) by 417 days.

(21) Appl. No.: 12/427,574

(22) Filed: Apr. 21, 2009

(65) Prior Publication Data
US 2010/0264921 A1    Oct. 21, 2010

(51) Int. Cl.
G01V 3/00    (2006.01)
(52) U.S. Cl. .................................................. 324/307
(58) Field of Classification Search .......... 324/300–322; 600/407, 410, 421
See application file for complete search history.

(56) References Cited

U.S. PATENT DOCUMENTS

| | | | |
|---|---|---|---|
| 5,635,834 A * | 6/1997 | Sloggett et al. | 324/248 |
| 6,185,810 B1 * | 2/2001 | Gubser et al. | 29/599 |
| 6,332,324 B1 * | 12/2001 | Saho et al. | 62/51.1 |
| 7,187,169 B2 * | 3/2007 | Clarke et al. | 324/307 |
| 7,218,104 B2 | 5/2007 | Clarke et al. | |
| 7,466,132 B2 * | 12/2008 | Clarke et al. | 324/318 |
| 7,482,804 B2 * | 1/2009 | Tilbrook et al. | 324/248 |
| 7,573,264 B2 * | 8/2009 | Xu et al. | 324/304 |
| 7,671,587 B2 * | 3/2010 | Penanen et al. | 324/300 |
| 2010/0109669 A1 * | 5/2010 | Penanen et al. | 324/318 |

OTHER PUBLICATIONS

K. Schlenga et al., Low-field magnetic resonance imaging with a high-Tc dc superconducting quantum interference device, Applied Physics Letter, Dec. 1999, pp. 3695-3697, vol. 75, No. 23.

Shu-Hsien Liao et al., Enhancement in low field nuclear magnetic resonance with a high-Tc superconducting quantum interference device and hyperpolarized 3He, Journal of Applied Physics, 2008, ppp. 63918-63918-5, vol. 104.

I. Sasada et al., Planar coil system consisting of three coil pairs for producing a uniform magnetic field, Journal of Applied Physics, 2006, pp. 904-904-3, vol. 99.

Wamquan Jiang et al., Preparation and properties of superparamagnetic nanoparticles with narrow size distribution and biocompatible, Journal of Magnetism and Magnetic Materials, 2004, pp. 210-221, vol. 283.

Robert McDermott et al., Liquid-State NMR and Scalar Couplings in Microtesla Magnetic Fields, Science, Mar. 22, 2002, pp. 2247-2249, vol. 295, No. 5563.

Shu-Hsien Liao et al., Longitudinal relaxation time detection using a high-Tc superconductive quantum interference device magnetometer, Journal of Applied Physics, 2007, pp. 033914-033914-4, vol. 102, Issue 3.

Shu-Hsien Liao et al., Characterization of magnetic nanoparticles as contrast agents in magnetic resonance imaging using high-Tc superconducting quantum interference devices in microtesla magnetic fields, Superconductor Science and Technology, 2009, pp. 1-5, vol. 22, IOP 1 Publishing Ltd., United Kingdom.

* cited by examiner

*Primary Examiner* — Brij Shrivastav
(74) *Attorney, Agent, or Firm* — WPAT, P.C.; Anthony King

(57) ABSTRACT

The invention provides a high resolution proton nuclear magnetic reonance and imaging (NMR/MRI) in microtesla magnetic fields by using high critical temperature (high-$T_c$) superconducting quantum interference device (SQUID) magnetometer via a flux transformer. Both the SQUID and the input coupling coil are installed inside a superconducting vessel which shields environmental noise and set the SQUID in a stable operation condition. The present invention also offers the advantages of preserving the NMR signal even if the sample is far away from the SQUID detector.

6 Claims, 17 Drawing Sheets

(a)

$B_p$ = 450 gauss
$B_0$ = 101 $\mu$T
$G_y$ = 24.6 $\mu$T/m (b)

(c)

(a)

(b)

(c)

(a) (c) (d)

(b)

Side view

SQUID DETECTED NUCLEAR MAGNETIC RESONANCE AND IMAGING AT ULTRA-WEAK FIELDS

FIELD OF THE INVENTION

The invention relates to nuclear magnetic resonance (NMR) and magnetic resonance imaging (MRI), and more particularly to low noise NMR and MRI at ultralow magnetic fields using a high critical temperature (high-$T_c$) superconducting quantum interference device (SQUID) spectrometer coupled with a flux transformer.

BACKGROUND OF THE INVENTION

Nuclear magnetic resonance (NMR) is the name given to a physical resonance phenomenon involving the observation of specific quantum mechanical magnetic properties of an atomic nucleus in the presence of an applied, external magnetic field. Many scientific techniques exploit NMR phenomena to study molecular physics, crystals and non-crystalline materials through NMR spectroscopy. NMR is also routinely used in advanced medical imaging techniques, such as in magnetic resonance imaging (MRI).

A superconducting quantum interference device (SQUID) is a sensitive detector which is used to measure extremely weak signals, such as subtle changes in the human body's electromagnetic energy field based on the quantum mechanical Josephon effect. A Josephson junction is made up of two superconductors, separated by an insulating layer so thin that electrons can tunnel through. A SQUID consists of tiny loops of superconductors employing Josephson junctions to achieve superposition: each electron moves simultaneously in both directions. Because the current is moving in two opposite directions, the electrons have the ability to perform as qubits (that theoretically could be used to enable quantum computing). SQUIDs have been used for a variety of testing purposes that demand extreme sensitivity, including engineering, medical, and geological equipment.

Both the low field NMR and MRI are based on SQUID, which can avoid the drawbacks of high-field NMR and MRI such as susceptibility artifacts, the cost issue, the size and complexity of the high-field system and so on. The demand of the field homogeneity is not as strict as that of high field NMR/MRI although the signal-to-noise ratio (SNR) is weak in low field NMR/MRI. A homogeneity of 1 part per $10^4$ in the magnetic field can reach a line width of 0.426 Hz in the NMR spectrum. Therefore, the construction of a low field spectrometer of high spectral resolution is much easier than that of the high field NMR/MRI.

The detection sensitivity of NMR/MRI using SQUID designed to image small samples was reported in reference, e.g. K. Schlenga et al., "Low-field magnetic resonance imaging with a high-$T_c$ dc superconducting quantum interference device," Appl. Phys. Lett. 75, 3695 (1999). For most studies, un-tuned SQUID were used and the samples were mounted under the cryostat with the distance between the sample and detector kept as close as possible because the signal can decay quickly when the distance between sample and detector is increased. It has been demonstrated that the sensitivity decreases rapidly as the separation between the SQUID and the sample increases beyond a certain value. A simple calculation shows that the signal will be reduced by a factor of two as the distance from the SQUID is varied from 1 mm to 50 mm, see S. H. Liao et al., "Enhancement in low field nuclear magnetic resonance with a high-$T_c$ superconducting quantum interference device and hyperpolarized $^3$He," J. Appl. Phys. 104, 063918 (2008). However, there are many circumstances in which it is impratical to keep the samples close to the detector.

U.S. Pat. No. 7,218,104 disclosed a method and an apparatus for the detection of NMR signals and production of MRI by obtaining NMR spectra of liquids in microtesla field using prepolarization in millitesla fields and detection with an untuned dc low critical temperature (low-$T_c$) SQUID. Because the sensitivity of the SQUID is frequency independent, both SNR and spectra resolution are enhanced by detecting the NMR signal in extremely low magnetic fields, where the NMR lines become very narrow for grossly inhomogeneous measurement fields. The detector is a SQUID magnetometer designed so that the SQUID detector can be very close to the sample, which is at room temperature. However, the SQUID magnetometer is so sensitive that when applying magnetization field or RF pulse to the sample, it may affect the SQUID.

SUMMARY OF THE INVENTION

The present invention provides a method for detecting nuclear magnetic resonance (NMR) of a sample, comprising: (a) pre-polarizing nuclear spins in the sample in a millitesla magnetic field or higher than 10 mT; (b) detecting nuclear magnetic resonance (NMR) signals from the sample in a microtesla magnetic field with a high critical temperature (high-$T_c$) superconducting quantum interference device (SQUID) magnetometer via a flux transformer consisting of a pickup coil and an input coil, wherein the SQUID and the input coil are installed inside a superconducting vessel.

The present invention further provides an apparatus for detecting nuclear magnetic resonance (NMR) of a sample, comprising: (a) a pre-polarization coil for providing a millitesla magnetic field for prepolarizing nuclear spins in the sample; (b) a flux transformer consisting a pickup coil and an input coil, wherein the pickup coil is fitted into the pre-polarization coil; and (c) an high critical temperature ($T_c$) superconducting quantum interference device (SQUID) magnetometer for detecting nuclear magnetic resonance (NMR) signals from the sample, wherein the SQUID and the input coil are installed inside a superconducting vessel.

DETAILED DESCRIPTION OF THE INVENTION

Figure 1:
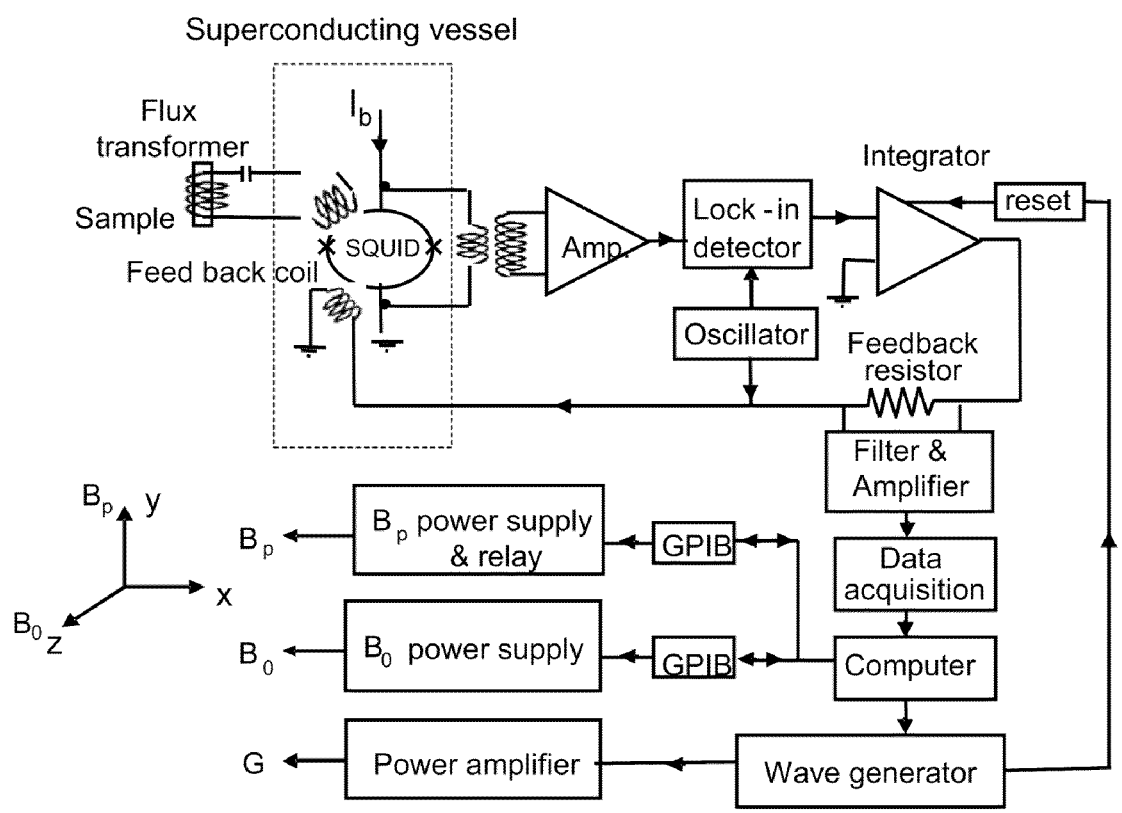
FIG. 1 shows schematic of a high-$T_c$ SQUID-based NMR detection apparatus.

The invention is directed to certain improvements in NMR/MRI as described herein, and other aspects of the NMR/MRI systems are conventional and not described since they are well known in the art.

The present invention provides a method for detecting nuclear magnetic resonance (NMR) of a sample, comprising: (a) pre-polarizing nuclear spins in the sample in a millitesla magnetic field or higher than 10 mT; (b) detecting nuclear magnetic resonance (NMR) signals from the sample in a microtesla magnetic field with a high critical temperature (high-$T_c$) superconducting quantum interference device (SQUID) magnetometer via a flux transformer consisting of a pickup coil and an input coil, wherein the SQUID and the input coil are installed inside a superconducting vessel.

The invention also provides an apparatus for detecting nuclear magnetic resonance (NMR) of a sample, comprising: (a) a pre-polarization coil for providing a millitesla magnetic field or higher than 10 mT for prepolarizing nuclear spins in the sample; (b) a flux transformer consisting a pickup coil and an input coil, wherein the pickup coil is fitted into the pre-polarization coil; and (c) an high critical temperature ($T_c$) superconducting quantum interference device (SQUID) magnetometer for detecting nuclear magnetic resonance (NMR) signals from the sample, wherein the SQUID and the input coil are installed inside a superconducting vessel.

In this invention, the spin procession of proton is inductively coupled to the SQUID spectrometer. Coupling is accomplished through a flux transformer with both the SQUID and input coupling set up in a superconducting vessel, which allows avoidance of environmental noises and sets the SQUID in a stable operation. The flux transformer, which consists of a pickup coil and an input coil connected to a capacitor and an inductance to form a NMR resonance circuit, is tuned to the nuclear resonance frequency of to-be-detected samples in a measuring magnetic field of microtesla. This design, which uses resonance flux coupling, offers the advantages of preserving the SNR when the sample is a bit far away from the SQUID detector. The advantage is especially useful for imaging large samples when the required distance from the sample to the detector deteriorates the NMR signal. In an embodiment, the measuring magnetic field is from 1 to 200 μT, and in a more preferable embodiment, the measuring magnetic field is 101 μT. The direct-coupled high-$T_c$ SQUID magnetometer has a magnetic field resolution of 280 fT/$Hz^{1/2}$ at 4.3 kHz.

The term "superconducting vessel" used herein refers to a container which is made of superconductor. Superconductors are materials that have no resistance to the flow of electricity. Also, the magnetic field inside a bulk sample is zero (which is called the Meissner effect). When a magnetic field is applied current flows in the outer skin of the material leading to an induced magnetic field that exactly opposes the applied field. In a preferable embodiment, the superconducting vessel is composed of $Bi_2Sr_2Ca_2Cu_3O_y$.

The present invention using high critical temperature (high-$T_c$) superconducting quantum interference device (SQUID) requiring cooling with liquid nitrogen, which is much less expensive and easier to work with than using low critical temperature (low-$T_c$) SQUID which required cooling with liquid helium.

In the present invention, the sample is placed in the pre-polarization coil which can prepolarize the nuclear spins in a strong transient field to generate enhanced, nonequilibrium nuclear magnetization and thereby boost the strength of the NMR signal. The pickup coil and the unit which the pickup coil is fitted into the pre-polarization coil of the NMR detecting system. The pre-polarization coil is 1016 turns of wound copper coil capable of generating a pre-magnetic field in the range of about 10 mT or higher than 10 mT. In a preferable embodiment, the pre-magnetic field is 45 mT. The high-$T_c$ SQUID-based NMR spectrometer is set up in an electromagnetically shielded room. To produce a uniform magnetic field, a planar coil system consisting of three coil pairs is set up as Sasada I et al., "Planar coil system consisting of three coil pairs for producing a uniform magnetic field," J. Appl. Phys. 99, 08D904 (2006) disclosed. These three coil pairs are connected in series to produce a homogeneity better than 1 in $10^4$ over a sample column of 64 $cm^3$ at 101 μT. The static field $B_0$ of 101 μT is active along the z-axis, which is parallel to the plane of the high-Tc SQUID magnetometer. The pre-polarization field, Bp, of 45 mT is applied along the y-axis, which is also parallel to the plane of the SQUID magnetometer. Since the strength of the pre-polarization field is much higher than that of the measuring static field, the direction of nuclear spin magnetization of water is almost aligned along the y-axis of the pre-polarization field. After applying a prepolarization field for a duration time of $T_{Bp}$, the pre-polarization field is quenched after 3 ms. The precession of the nuclear magnetization is along the direction of Bo. The free induction decay (FID) signal of the proton spin is detected by a pick-up coil. The normal of the pick-up coil is along the z-axis direction and coupled to the high-Tc SQUID that is shielded within the superconducting vessel, and the output of the SQUID is amplified, integrated, and then fed back to a feedback coil positioned near the input coil of the SQUID in the superconucting vessel. NMR signals of the FID are filtered through band-pass filters. Then, one can obtain the NMR spectra through a fast Fourier transformation (FFT) and can also perform magnetic resonance imaging (MRI) of the sample by forming an image from the detected NMR signals.

The method of the present invention, wherein the sample can further introduce magnetic nanoparticles as a contrast agent into the sample to enhance NMR contrast. The magnetic fluids consisted of dextrane-coated magnetic nanoparticles dispersed uniformly in water, see Jiang W. et al., "Preparation and properties of superparamagnetic nanoparticles with narrow size distribution and biocompatible," 283, 210 (2004). The magnetic susceptibility of the magnetic fluid causes a dephasing of the proton nuclear spin, and a domination of the spin-spin and spin-lattice relaxation. Therefore, a broadening of the proton NMR spectra and increasing relaxation rate is observed when the $\chi$ value of the magnetic fluid is increased, and also an effective relaxation rate $\Gamma_{MF}$ can be observed due to the magnetic susceptibility of the magnetic fluid.

The method of the present invention, further comprising obtaining J-coupling information from the NMR signals. While all chemical shift information is lost in low magnetic field, J-coupling, which is field independent, is preserved.

The term "J-coupling" used herein refers to interaction between adjacent nuclear spins within a molecule. The effect is transmitted via the electrons in orbit around the nuclei. The behaviour of an individual spin is influenced by other coupled nuclei, their effect being to split what would otherwise be a single resonance into two or more distinct frequencies depending on the state of the coupled spin. This effect is useful in aiding the identification of particular species and for determining the molecular structures.

Both magnetic field noise inside the electromagnetically shielded room and the Johnson noise in the flux transformer will couple the field noise to high-$T_c$ SQUID via the flux transformer. In the present invention, the input coil is cooled to 77.4 K while the pickup coil is maintained at 300 K. The proposed cooled flux transformer couples Johnson noise, explained the relation: $<V^2>_{Johnson}=4 k_B TR\Delta f$ to the SQUID NMR spectrometer, where T is the temperature, R is the total resistance, and $\Delta f$ is the frequency of bandwidth. The resistance of the pickup coil $R_{pickup}$ is 4.5Ω at 300 K and the resistance of the input coil $R_{input}$ is 1Ω at 77.4 K. Therefore, Johnson noise $<V_2>^{1/2}_{Johnson}=2.91\times10^{-10}V/Hz^{1/2}$ exited in the flux transformer. The Johnson noise will couple a field noise of 187 fT/Hz$^{1/2}$ to SQUID. The noise is less compared to that in the high-$T_c$ SQUID magnetometer operating at the proton resonance frequency of 101 μT. High-$T_c$ supercondcting wires or cooled cryogenic flux transformer in gradiometer configuration can be used to further reduce the noise.

EXAMPLE

The examples below are non-limiting and are merely representative of various aspects and features of the present invention.

Example 1

Experimental Apparatus for NMR/MRI

As FIG. 1 showed, the high-$T_c$ SQUID-based NMR/MRI detection system was set up in an electromagnetically shielded room. The procession spin was inductively coupled to the SQUID magnetometer via a flux transformer consisting of a pickup coil and an input coil connected to a capacitor and an inductance to form a NMR resonance circuit. Besides, both the SQUID and the input coil were installed inside a superconducting $Bi_2Sr_2Ca_2Cu_3O_y$ vessel which not only shielded environmental noises but also set the SQUID in a more stable operation condition.

Figure 2:
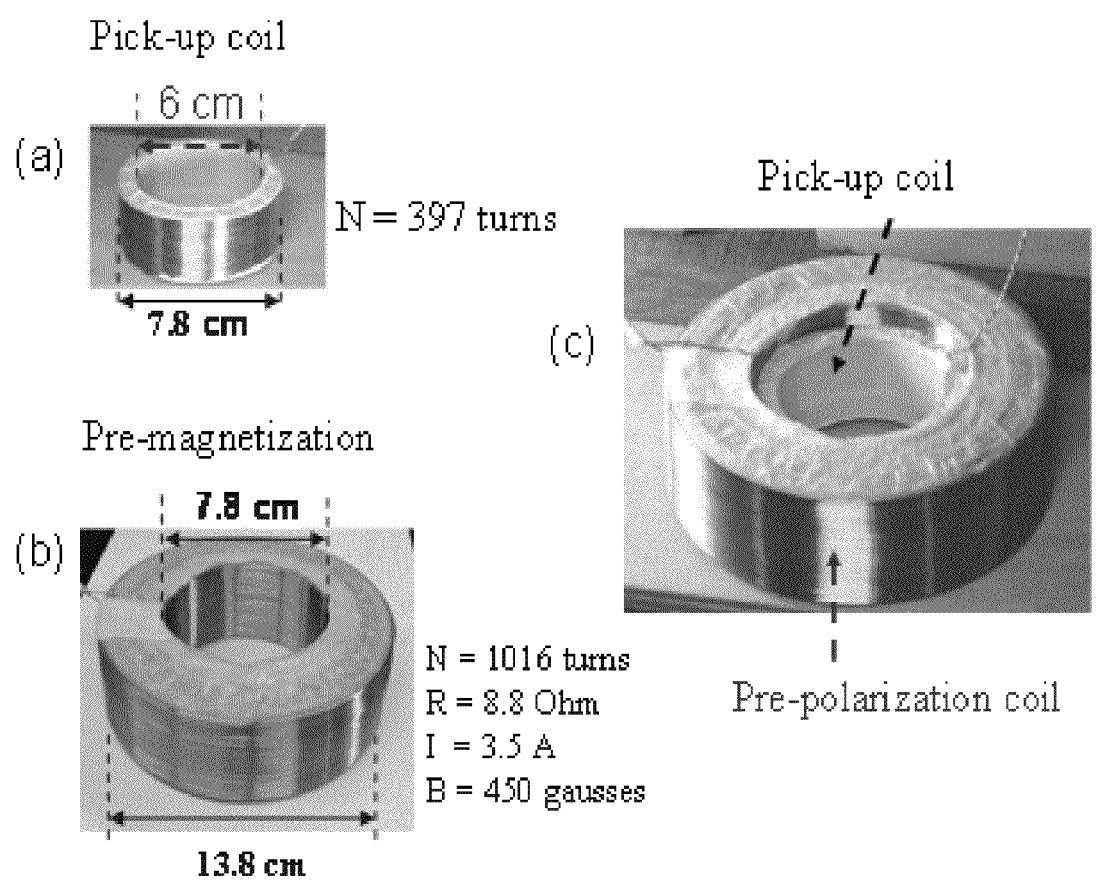
FIG. 2 shows photograph of (a) the pickup coil, (b) the pre-polarization coil, and (c) the pickup coil fitted into the pre-polarization coil.

FIG. 2 showed a photograph of the pre-polarization coil, the pickup coil and the unit which the pickup coil was fitted into the pre-polarization coil of the NMR detecting system. The pre-polarization coil was 1016 turns of wound copper coil capable of generating a pre-magnetic field of 450 gausses. The pickup coil composed of 397 turns of coils, in which the samples were placed, had an inner diameter of 6 cm and an outer diameter of 7.8 cm. The pickup coil was aligned along the z-axis direction and fitted into the pre-polarization coil. The input coil and the pickup coil formed a tank circuit and optimized the resonance frequency of proton. The directly coupled high-$T_c$ SQUID magnetometer showed a magnetic sensitivity of 280 fT/Hz$^{-1/2}$ at 4.3 kHz during NMR/MRI measurement.

Figure 3:
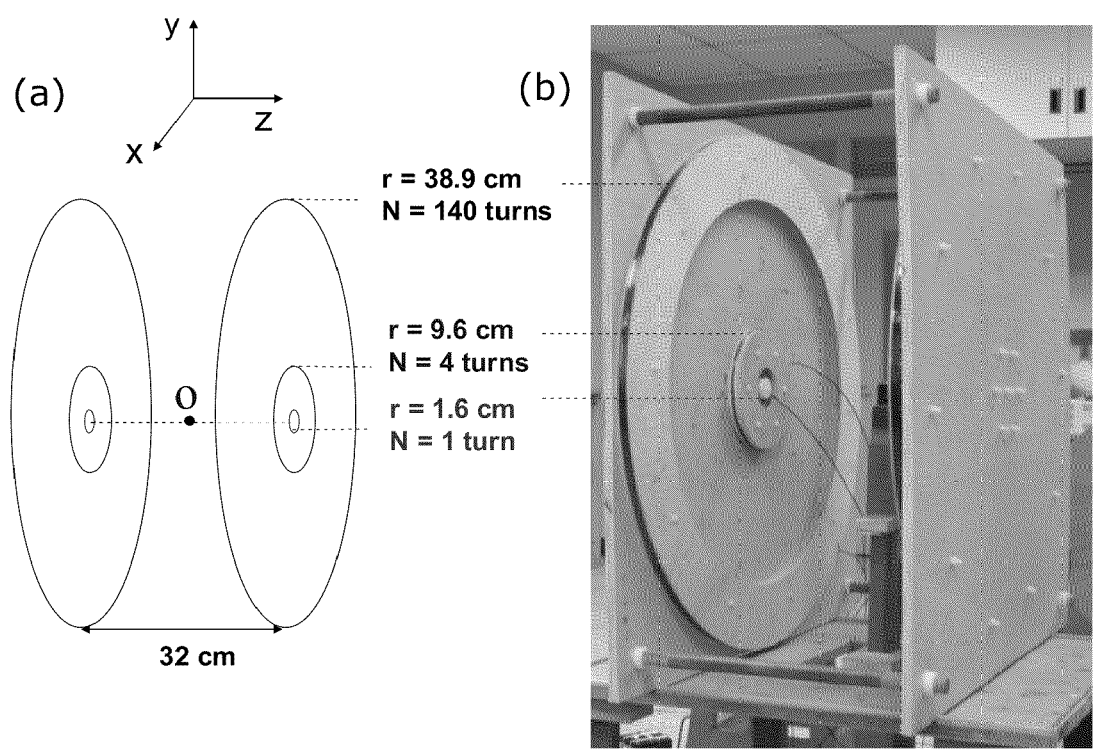
FIG. 3 shows (a) a planar coil system composed of three coil pairs, (b) a photograph of the coil system for producing uniform magnetic field.

FIG. 3 showed a planar measuring coil consisting of three coil pairs for the studies of NMR/MRI in low magnetic fields. The first coil pair had one turn with a radius of 1.6 cm, the second coil pair had four turns with a radius of 9.6 cm, and the third coil pair had wound 140 turns with a radius of 38.9 cm. These three coil pairs were connected in series to produce a homogeneity better than 1 in 10$^4$ over a sample column of 64 cm$^3$ at 101 μT.

Example 2

Microtesla Field NMR

Figure 4:
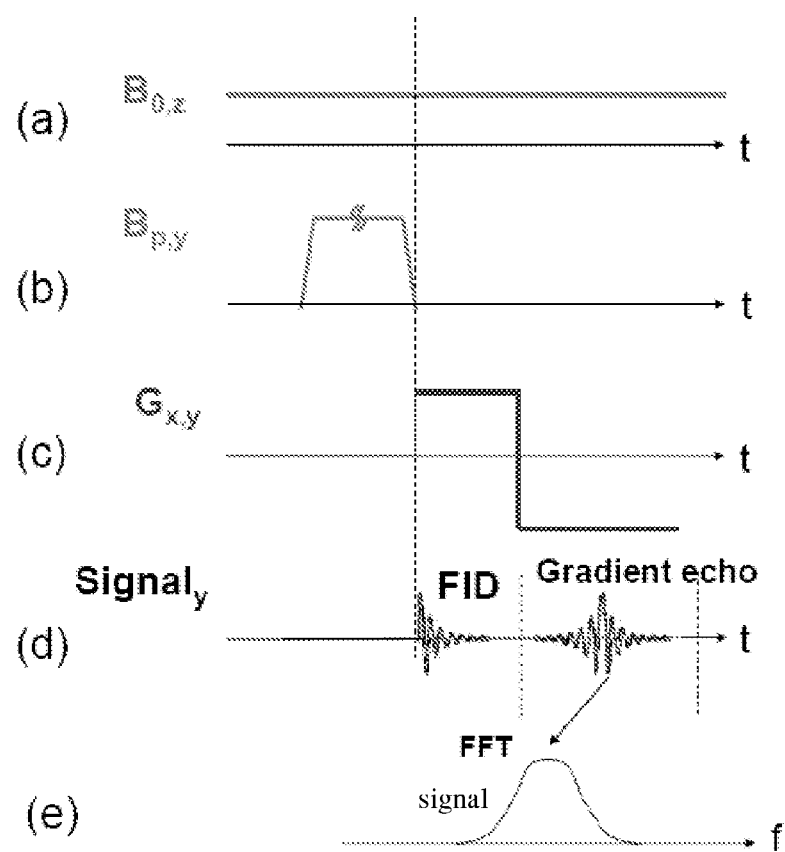
FIG. 4 shows sequences used in the NMR detection (a) the measuring field, (b) the pre-polarization field with a duration time $t_{BP}$, (c) the detected NMR signal as a function of time, and (d) the detected FID and spin echo signals as a function time.

FIG. 4 showed the sequence used in NMR/MRI measurements. The static measuring field $B_0$ of 101 μT was active along the z-axis direction, which was parallel to the plane of the SQUID magnetometer. A pre-polarization field $B_p$ of 45 mT was applied along the y-axis, which was parallel to the plane of the SQUID magnetometer. Since the strength of the pre-polarization field was much larger than that of the static measuring field, the direction of nuclear spin magnetization of proton was then approximately aligned along y-axis. After applying a polarization field for a short time of $T_{bp}$, the pre-polarization field was switched off in 3 milliseconds. The nuclear magnetization processed along the direction of the measuring field $B_0$. The gradient coils, which produced a gradient field of 24.6 μT/m for MRI, were constructed along the x-, y-, and z-directions. The MRI was taken using the back projection method with the applied gradient field rotated 15° for each imaging sequence.

Example 3

NMR/MRI Experiments

Figure 5:
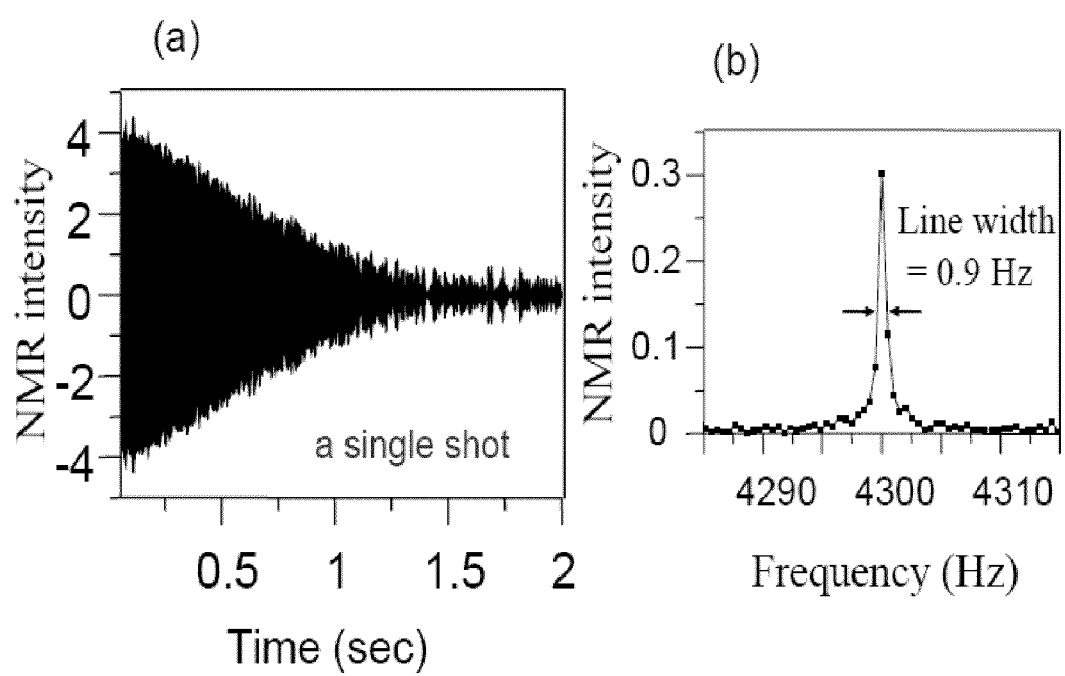
FIG. 5 shows (a) NMR intensity of 10 ml of pure water in a single shot, (b) Fourier transform of the NMR signal, and the line width is 0.9 Hz.

FIG. 5 showed a typical NMR signal and it's Fourier transformer for 10 ml of pure water. The SNR is 45 and the line width was 0.9 Hz, which was measured at 101 μT and a field of 1 part in 5×10$^3$ in one shot.

Figure 6:
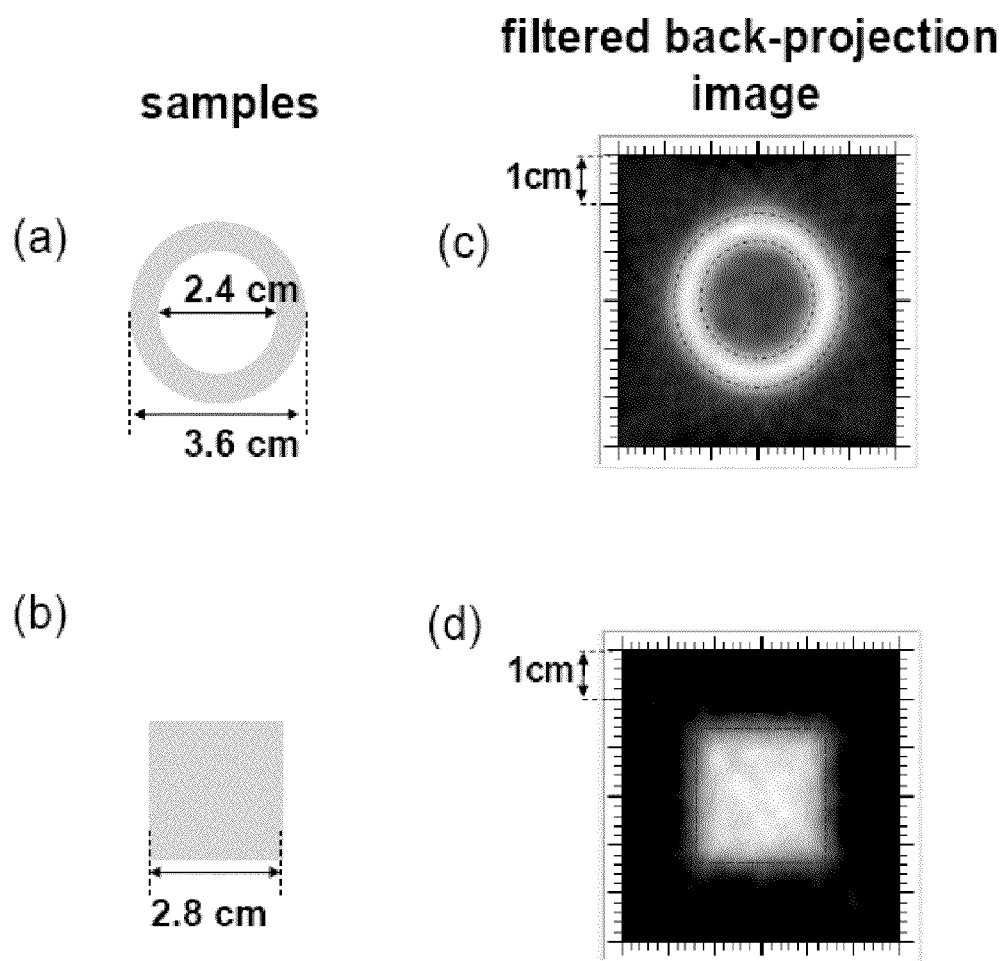
FIG. 6 shows (a) a ring-shape glass container filled with 10 ml of water, (b) its filtered MRI, (c) a rectangular-shape glass container filled with 10 ml of water and (d) its filtered MRI.

FIG. 6 showed the MRIs after 70 averages for a ring-shaped phantom and a rectangular-shaped phantom. Both phantoms were filled with 10 ml of water. The ring-shaped phantom had an inner diameter of 24 cm and an outer diameter of 36 mm, whereas the rectangular-shaped phantom had a width of 28 mm at each side. The image was taken with a gradient field of 24.6 µT/m along the direction using the back projection technique. The filter back projection MRIs showed a clear image contrast. The dash line marked in the image was the geometry of phantoms under investigation.

Figure 7:
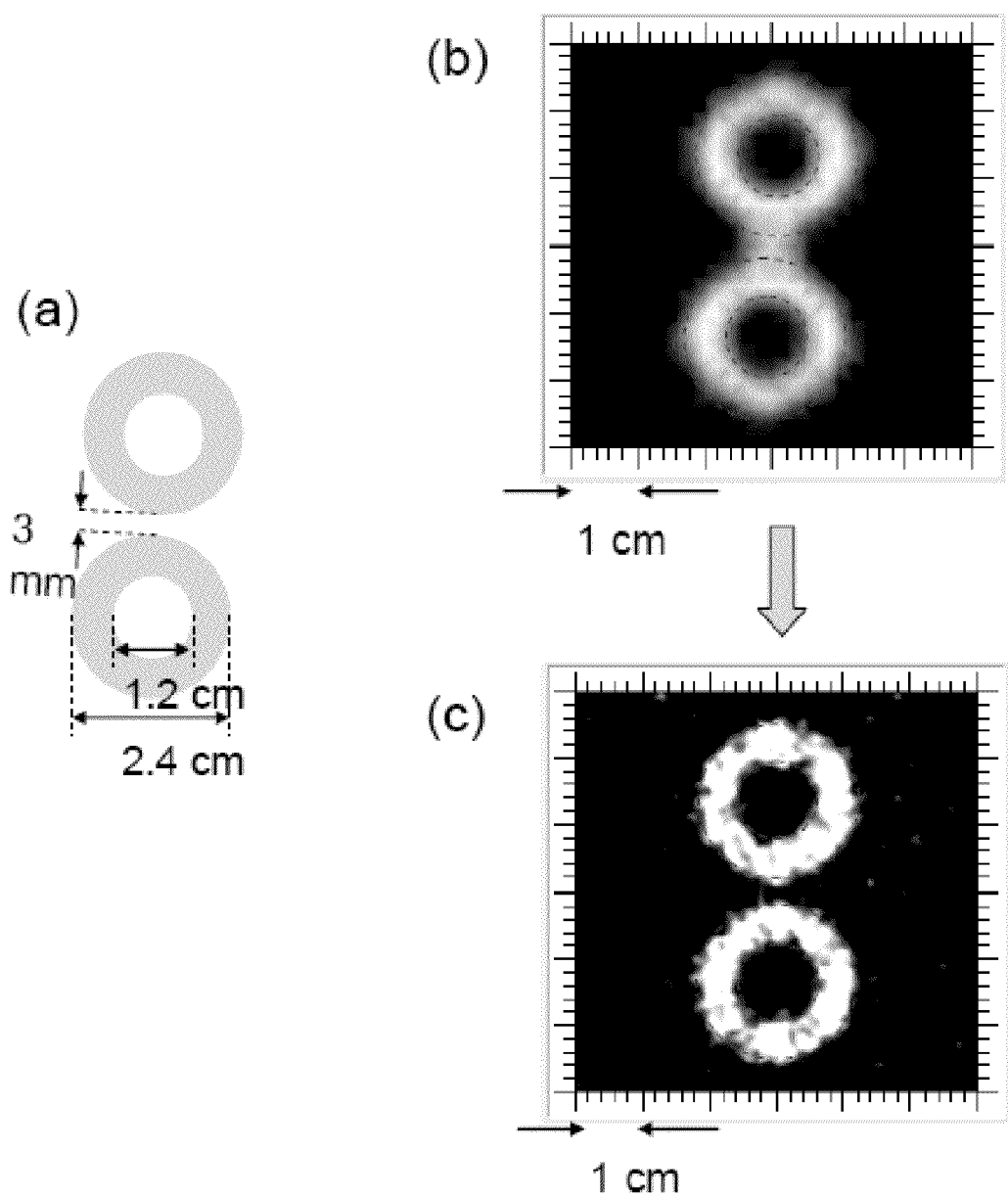
FIG. 7 shows (a) two hollow cyclinders containing of water of 9 ml, each are separated by a distance of 3 ml, and MRIs taken in a field uniformity of (b) one part in $1\times10^3$ and (c) 1 part in $5\times10^3$.

FIG. 7 showed two cylindrical ring phantoms separated by a distance of 3 mm. Each ring phantom had an inner diameter of 12 mm, and outer diameter 24 mm and a height of 2.2 mm and contained 10 ml of pure water. The imaged of ring phantoms taken in a field uniformity of one part in $10^3$, shown in FIG. 7(b), can be resolved at the center region, while the images taken in a filed uniformity of 1 part per $5\times10^3$ can clearly be resolved as shown in FIG. 7(c). The spatial resolution $\Delta x$ is given by $\Delta x=2\pi\Delta f/\gamma G$, where $\gamma=42.58$ kHz/mT and the gradient field $G=24.6$ µT/m in measurement. A line width $\Delta f=0.9$ Hz in a field uniformity of 1 part in $5\times10^3$ and $\Delta f=3$ Hz in a field of uniformity of one part in $10^3$ were observed. A spatial resolution $\Delta x=1$ and 3 mm, respectively, in the MRIs were expected. This analysis explained that the images shown in FIG. 7(b) cannot be resolved, whereas the images shown in FIG. 7(c) can clearly be resolved.

Figure 8:
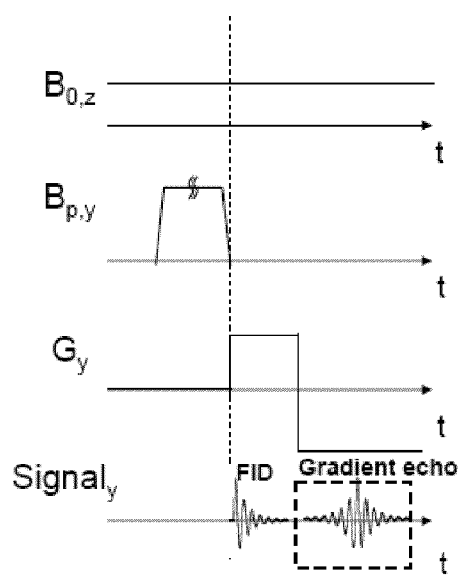
FIG. 8 shows (a) the sequences used in NMR/MRI measurements, (b) two hollow cylindrical containers containing of water with the small cylinder piled on top of the larger one and (c) the corresponding Fourier transform of the NMR signal.
Figure 8:
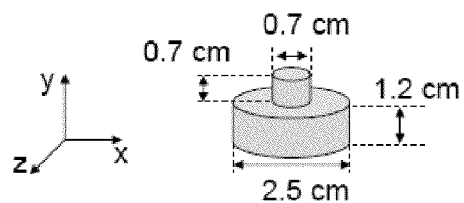
Figure 8:
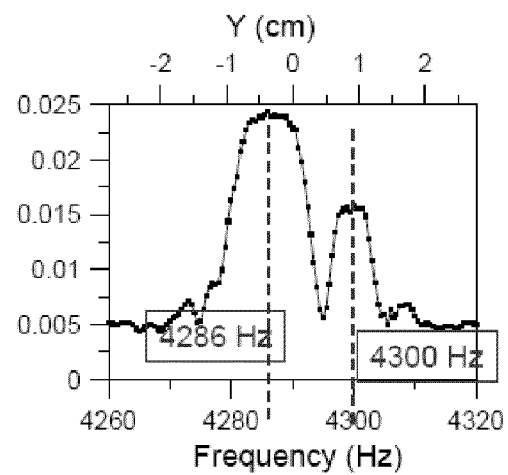
Figure 9:
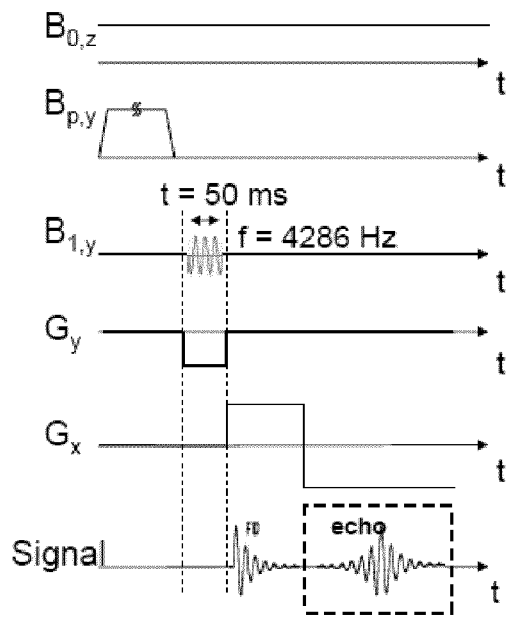
FIG. 9 shows (a) the sequences used in NMR/MRI measurements, (b) the filtered tomographica MRI image of the large cylindrical container and (c) Fourier transform for the image shown in (b).
Figure 9:
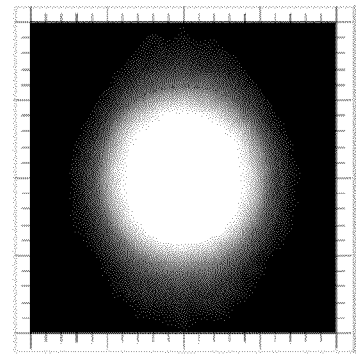
Figure 9:
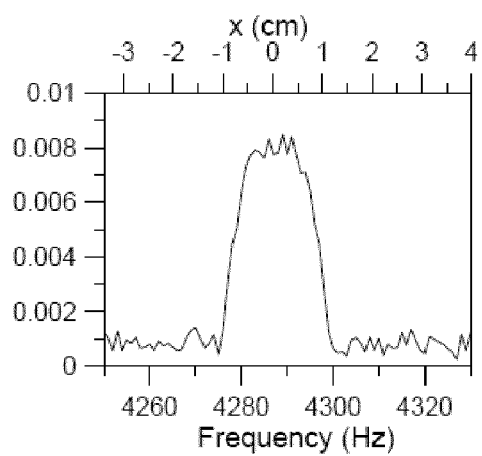
Figure 10:
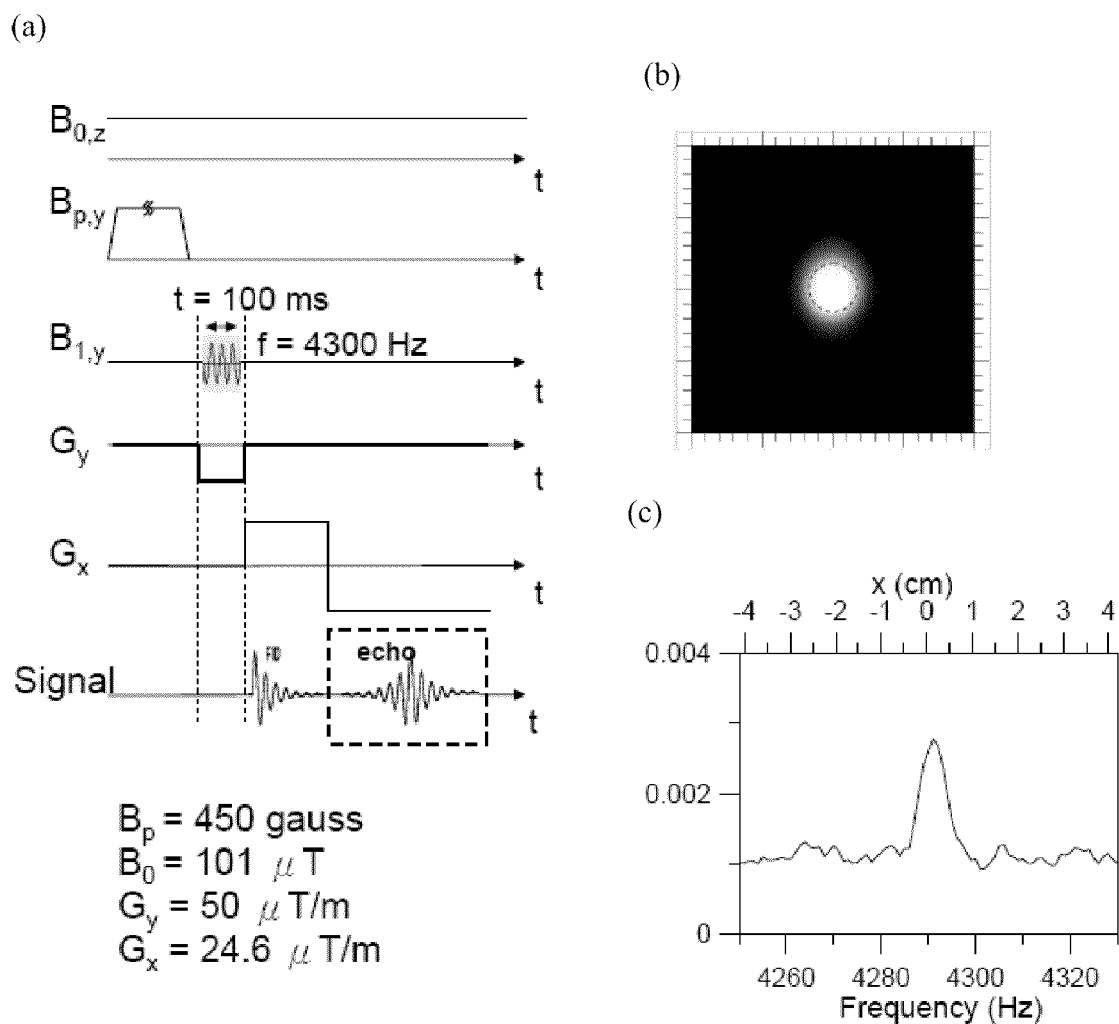
FIG. 10 shows (a) the sequences used in NMR/MRI measurements, (b) the filtered tomographical MRI image of the small cylindrical container and (c) Fourier transform for the image shown in (b).
Figure 11:
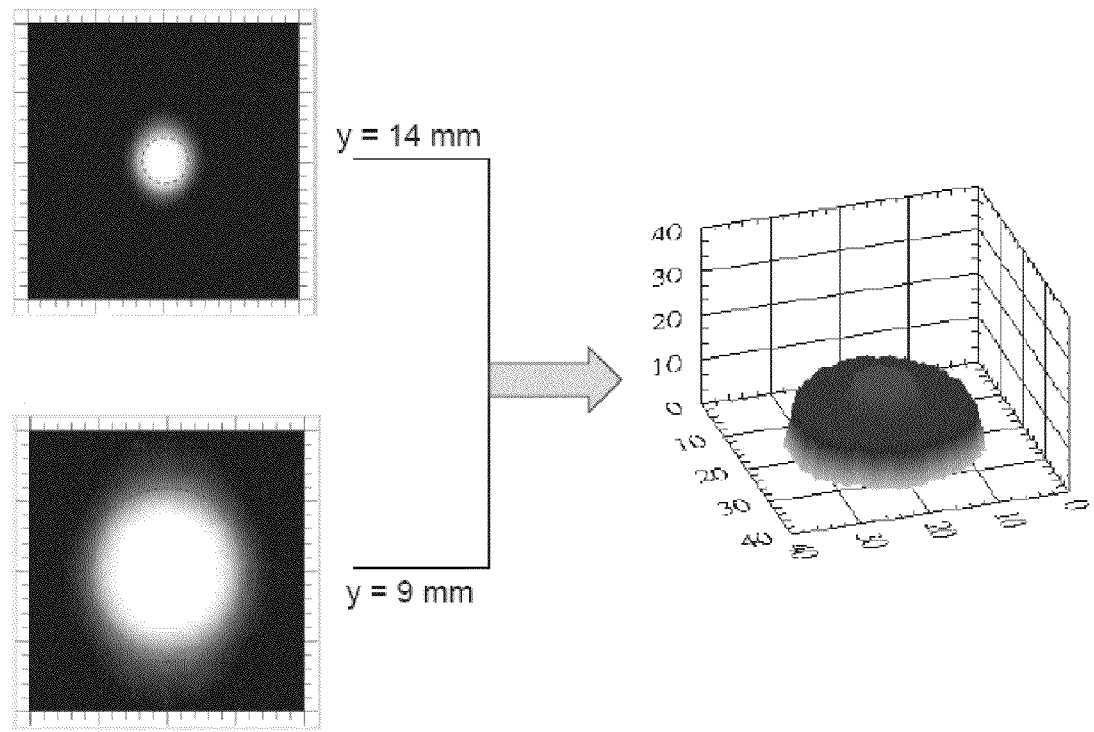
FIG. 11 shows the two tomographic MRI images are superimposed and registered and aligned to form a 3D MRI image.

FIG. 8(a), FIG. 9(a) and FIG. 10(a) showed the sequence used in NMR/MRI measurements as example 2 mentioned. FIG. 8(b) showed schematic of an object used in the 3D MRI experiment, wherein the object was composed of two hollow cylindrical containers containing of water with the small cylindrical container piled on top of the larger one. The small cylindrical container had a diameter of 0.7 cm and a height of 0.7 cm, whereas the large cylindrical container had a diameter of 2.5 cm and a height of 1.2 cm. FIG. 8(c) showed the corresponding Fourier transform of the NMR signal. FIGS. 9(b) and 9(c) showed the filtered tomographica MRI image of the large cylindrical container and the Fourier transform for the image shown in (b), respectively. FIGS. 10(b) and 10(c) showed the filtered tomographical MRI image of the small cylindrical container and the Fourier transform for the image shown in (b), respectively. These two tomographic MRI images were using computer calculation to be joined together to produce a 3-dimensional model as FIG. 11 shown, indicating that the invention can also use in 3D MRI field in ultra weak field.

Figure 12:
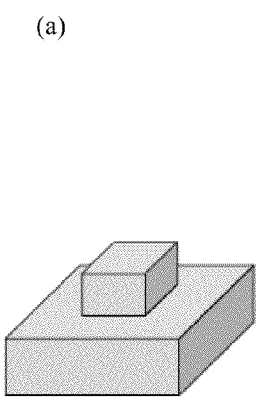
FIG. 12 shows (a) schematic of a cubical container containing of water piled on top of a rectangular-shape container, (b) side view of (a) wherein dotted line represents cross-sections, (c) tomographical MRI images of the five cross-sections and (d) the five tomographic MRI images are superimposed and registered and aligned to form a 3D MRI image.
Figure 12:
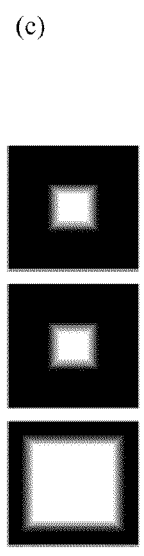
Figure 12:
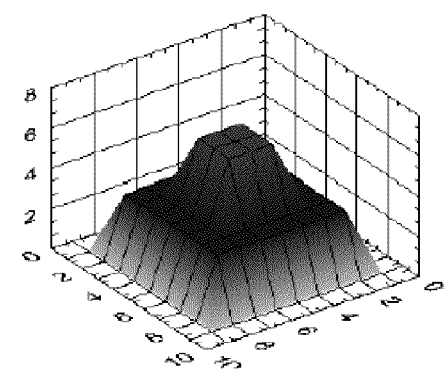
Figure 12:
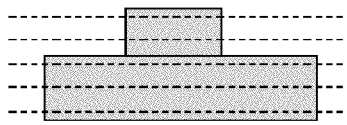

FIG. 12(a) further showed a schematic of a cubical container containing of water piled on top of a rectangular-shape container, and its side view as FIG. 12(b) showed, wherein dotted line represents five cross-sections scanned by MRI, and FIG. 12(c) were the tomographical MRI images of the five cross-sections. The five tomographic MRI images were superimposed and registered and aligned to form a 3D MRI image as FIG. 12(d) showed indicating that the low noise NMR and MRI at ultralow magnetic fields using a high-$T_c$ SQUID spectrometer of this invention can prompt more accurate diagnoses and enhanced healthcare.

Example 4

Detection of J-coupling

Considering the NMR spectrum of trimethyl phosphate $((CH_3O)_3PO)$ that shows a J-coupling between phosphate ($^{31}P$) nucleus and proton ($^1H$) nucleus, the Hamiltonian for the spin of proton in a magnetic field $B_0$ can be expressed as:

$$H_H = -h_{\gamma H} S_H (B_0 - 2\pi J \Sigma_i m_{Pi}/\gamma H) \quad (1)$$

Where $\gamma H$ and $S_H$ are the gyromagnetic ratio and the nuclear spin of proton respectively, J is the scalar coupling constant and $m_p$ is the z-component of phosphate nuclear spin. This means that the action of $^{31}P$ nucleus on $^1H$ nucleus is like an additional magnetic field with a magnitude of $2\pi Jm_{Pi}/\gamma H$ at the position of proton nucleus. This field corresponds to the magnetic field that was induced by the electron cloud by the $^{31}P$ nucleus.

Figure 13:
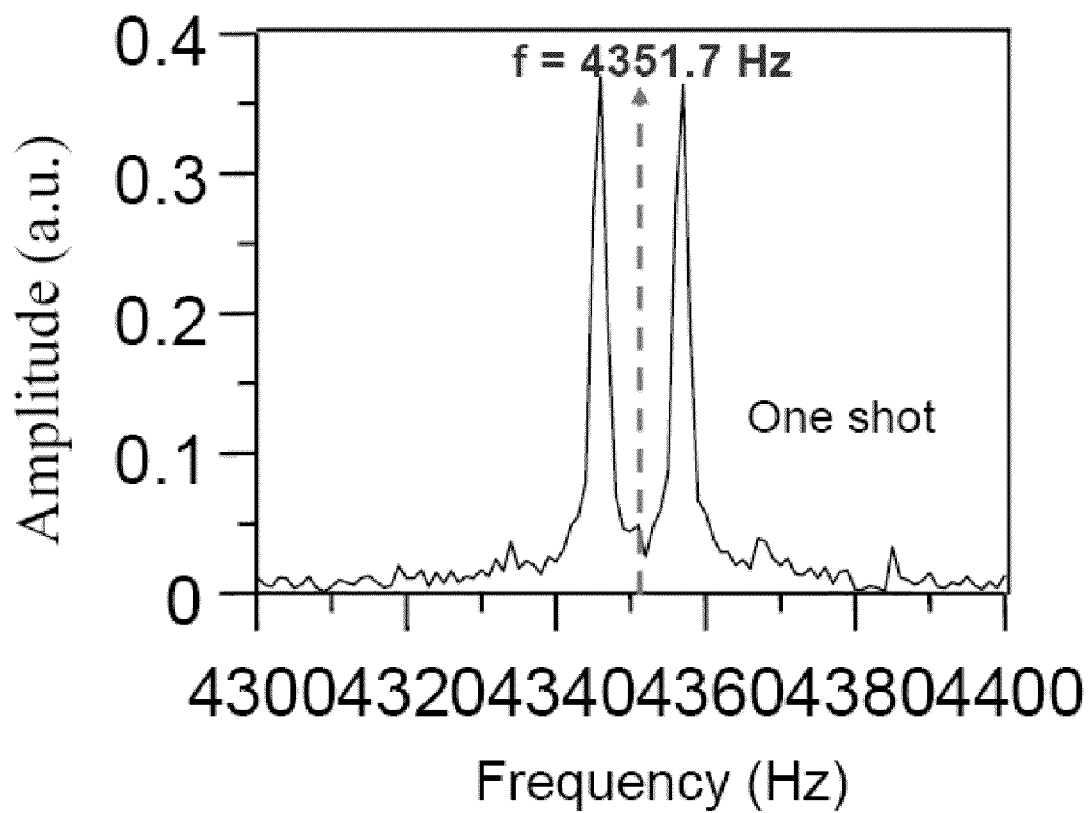
FIG. 13 shows NMR spectrum of trimethyl phosphate in one shot.

The enhanced spectral resolution and NMR signals can be exploited to detect the scalar coupling in heteronuclear spin system. In FIG. 13, that the NMR spectrum of trimethyl phosphate one shot and the spectrum showed a high SNR of 29.1. The gyromagnetic factor of protein ($^1H$) as known to be 42.58 kHz/mT, which corresponded to a resonance frequency of 4351.7 Hz in an experimental magnetic field of 102.2 µT. Electron-mediated scalar coupling of the nine equivalent protons to $^{31}P$ splitted the proton resonance into a doublet. The peaks arounded the vally were due to the electron mediated indirect phosphate-spin and proton-spin interaction $J_3[P,H]=(10.94\pm0.08)$ Hz. Scalar coupling to the nine protons splitted the $^{31}P$ resonance into lines were below the noise level and were not observed in experiments. It had been reported the scalar coupling $J_3[P,H]=(10.94\pm0.6)$ for trimethyl phosphate using low-$T_c$ SQUID in 4.8 µT. The NMR spectrum was the average of 100 transients, see McDermott R. et al., "Liquid-State NMR and Scalar Couplings in Microtesla Magnetic Fields," Science 295, 2247, (2002). The magnetic field $B_0$ applied in FIG. 8 was a little bit higher than that used in FIG. 5 due to a difference in the output current from the power supply. The molecular weight of trimethyl phosphate was 140.1 (density=1.2 g/ml) whereas that of pure water (density=1) was 18. For the same volume of trimethyl phosphate and pure water in experiments fewer amount of protons in trimethyl phosphate was contributed in NMR signals compared with that of water. Therefore the NMR signal detected in trimethyl phosphate showed a smaller SNR compared with that of pure water. In the present invention, it showed a high-sensitivity J coupling in one shot by using the apparatus of the invention.

Example 5

Use Magnetic Nanoparticles as Contrast Agents

Figure 14:
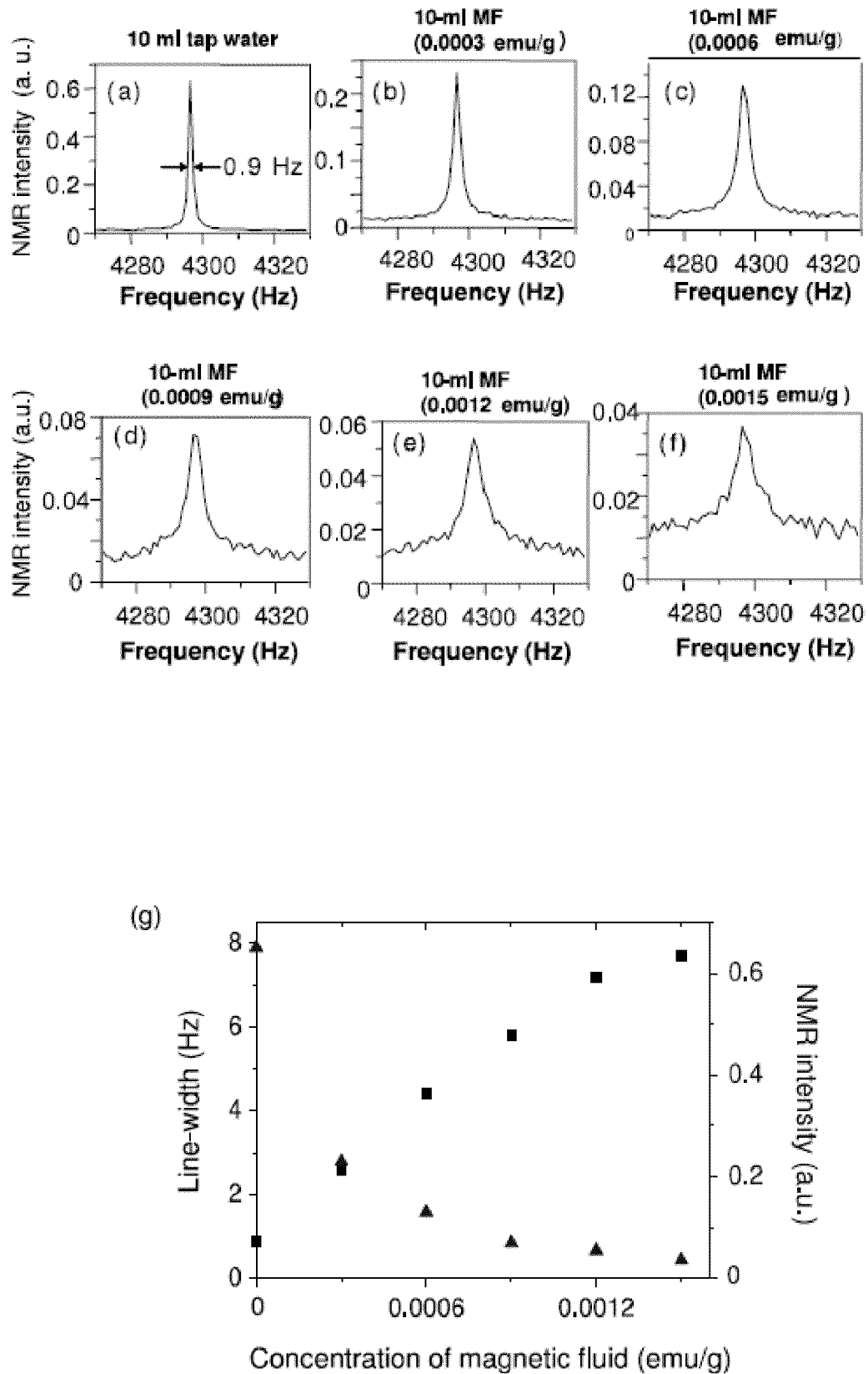
FIG. 14 shows the NMR intensity for (a) water, the NMR intensity magnetic fluids with different $\chi$ values: (b) 0.0003, (c) 0.0006, (d) 0.0009, (e) 0.0012, and (f) 0.0015 emu $g^{-1}$, respectively, and (g) shows the dependence of the linewidth on the magnetic susceptibility, square represents the linewidth, and triangle represents the NMR intensity.

FIG. 14(a) depicted the NMR intensity of water, and FIGS. 14(b), (c), (d), (e), and (f) depicted the NMR intensity of magnetic fluids as a function of magnetic concentrations of 0.0003, 0.0006, 0.0009, 0.0012, and 0.0015 in units of emu $g^{-1}$, respectively. The magnetic fluids consisted of dextran-coated magnetic nanoparticles dispersed uniformly in water. The size of the magnetic nanoparticles was 30 nm in diameter. The linewidth of the NMR spectrum was 1 Hz, with a SNR of 45 in a single shot. The intensity of the proton NMR signal decreased as the magnetic concentration ($M_s$) of the magnetic fluids increased. The magnetic concentration $M_s$ rescued the intensity of the NMR signal and caused the linewidth to broaden. FIG. 14(g) depicted the linewidth of the NMR spectra and the intensity as a function of the concentration of the magnetic fluid. The magnetism of the magnetic fluids deteriorated the homogenisity of the field which caused the dephasing of the proton nuclear spin, and the domination of the spin-spin and spin-lattice relaxation. Therefore, a broadening of the proton NMR spectra and growing relaxation rate were observed when the $M_s$ of the magnetic fluids was increased.

Figure 15:
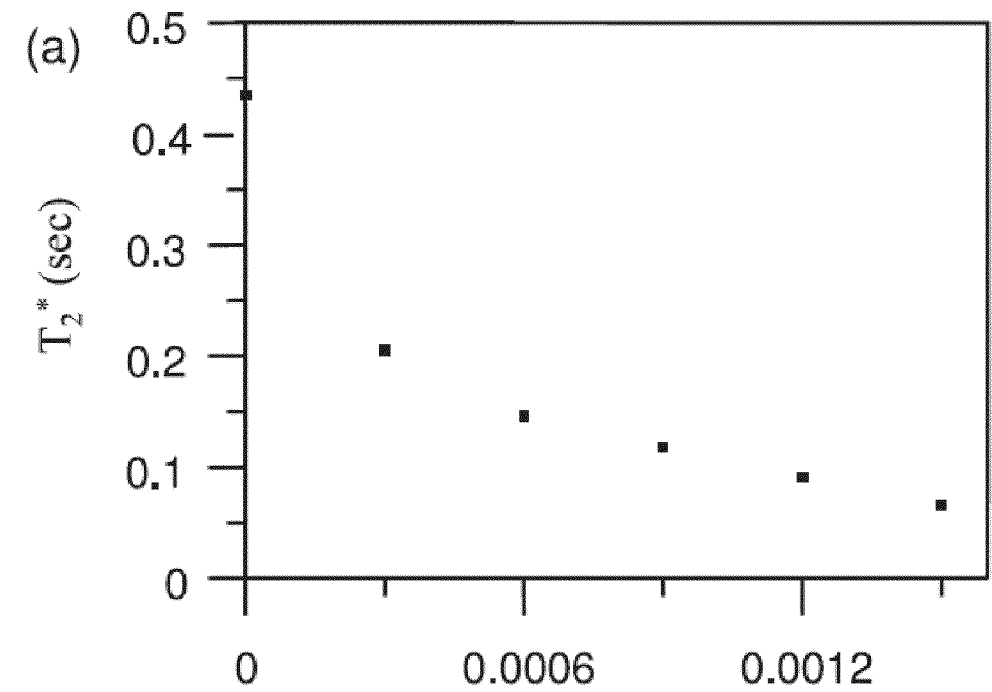
FIG. 15 shows (a) $T^*_2$ and (b) $\Gamma_{MF}$ of the magnetic fluids as a function of $\chi$ in units of emu $g^{-1}$.
Figure 15:
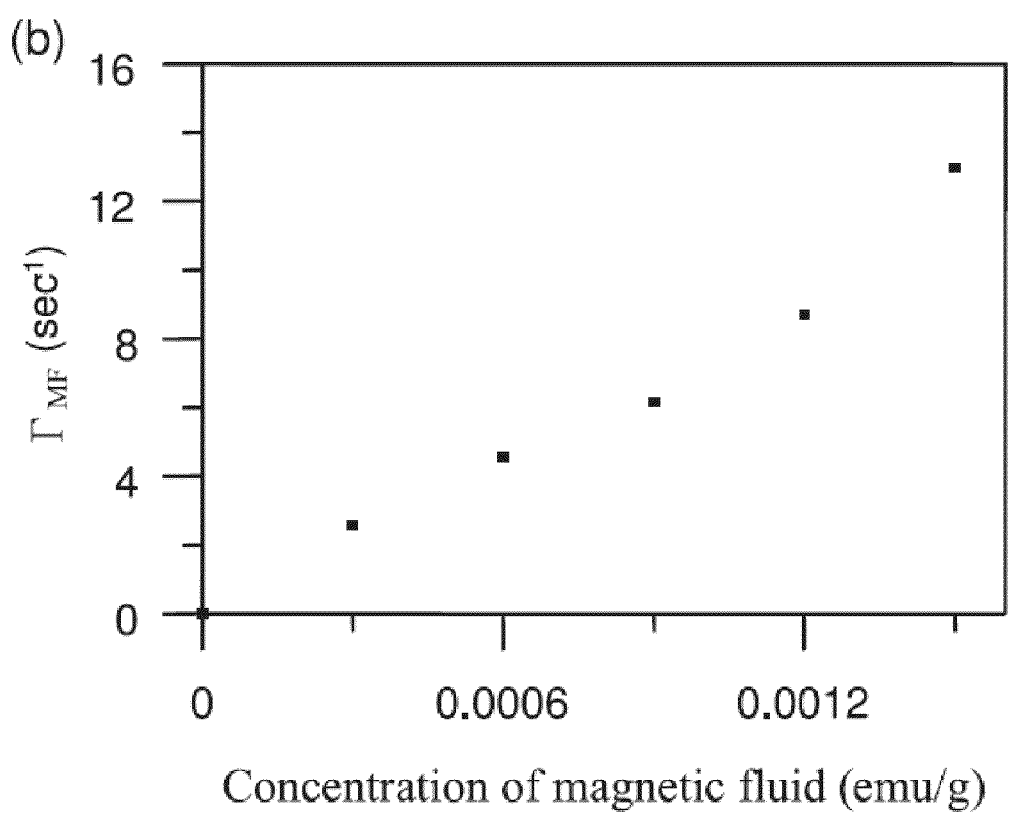

FIG. 15(a) showed the transverse spin-spin relaxation time, $T^*_2$, as a function of $M_s$ in units of emu $g^{-1}$. $T^*_2$ is determined from the equation $$M(t)=M_0 \exp(-t/T^*_2), \quad (2)$$

where M(t) is magnetization of samples at the instant of time t, $M_0=M$ (t=0), and $T^*_2$ is the total relaxation time. $T^*_2$ is related to the inhomogeneity parameter $\Gamma_{inhomogeneity}$ of the magnetic fields by the following equation:

$$\frac{1}{T_2^*} = \frac{1}{T_2} + \Gamma_{inhomogeneity}, \qquad (3)$$

where $\Gamma_{inhomogeneity}$ was the effective relaxation rate, which was caused by the inhomogeneity of the measuring magnetic field. $T^*_2$ decreased from 0.43 to 0.07 s when the $M_s$ of the magnetic fluids increased from 0 (pure water) to 0.0015 emu $g^{-1}$. The magnetic fluids affected the relaxation time $T^*_2$ through the equation $$\frac{1}{T_2^*} = \frac{1}{T_2} + \Gamma_{inhomogeneity}, + \Gamma_{MF} \qquad (4)$$

where $\Gamma_{MF}$ was the relaxation rate due to the magnetism caused by the magnetic fluid. Equation (3) represented the effects of the inhomogeneity of the magnetic field on the relaxation time $T_2$. In addition to the effect of the field homogeneity, equation (4) showed that the magnetism of magnetic fluid will introduce additional effects to the relaxation time $T_2$. In NMR measurements, the field Bo was kept at 101 μT; hence, $\Gamma_{inhomogeneity}$ remained the same value. From equations (2) to (4), we can derive $\Gamma_{MF}$ as a function of $M_s$ from the measured $T^*_2$. FIG. 10(b) showed the derived values of $\Gamma MF = 1/T_{MF}$ as a function of the $M_s$ in units of emu $g^{-1}$, where $T_{MF}$ was the effective relaxation time (in seconds) of the magnetic fluids. It was observed that $\Gamma_{MF}$ increased from 0 to 13.5 $s^{-1}$ when the $M_s$, relative to water, increased from 0 to 0.0015 emu $g^{-1}$. Both the $M_s$ of magnetic fluid and the inhomogeneity of the fields caused the proton nuclear spin to dephase and reduced the spin-spin relaxation time. The longitudinal relaxation time $T_1$ was investigated, see Liao S H et al., "Longitudinal relaxation time detection using a high-$T_c$ superconductive quantum interference device magnetometer" J. Appl. Phys. 102, 033914 (2007), and $T_1$ was estimated to be (2.11±0.04) s at 24° C. in a measuring field of 95 μT via the equation $$M(t) = S_o(1 - e^{-tBp/T_1}), \qquad (5)$$

where $S_o$ was the NMR intensity at saturation and $t_{Bp}$ was the pre-polarization time in NMR measurements. By using the same method, the NMR signal was measured as a function of $T_{Bp}$ and derived $T_1 = 140$ ms for magnetic fluids with $M_s = 0.0006$ emu $g^{-1}$. It was found that $T_1$ decreased significantly as the value of $M_s$ of the magnetic fluids was increased from 0 to 0.0006 emu $g^{-1}$. The decreased $T_1$ can be attributed to magnetic dipole-dipole interaction. A sufficient impact of the thermal noise due to random collisions between the ferromagnetic grains and the molecules of the carrier liquids induces fluctuations.

Figure 16:
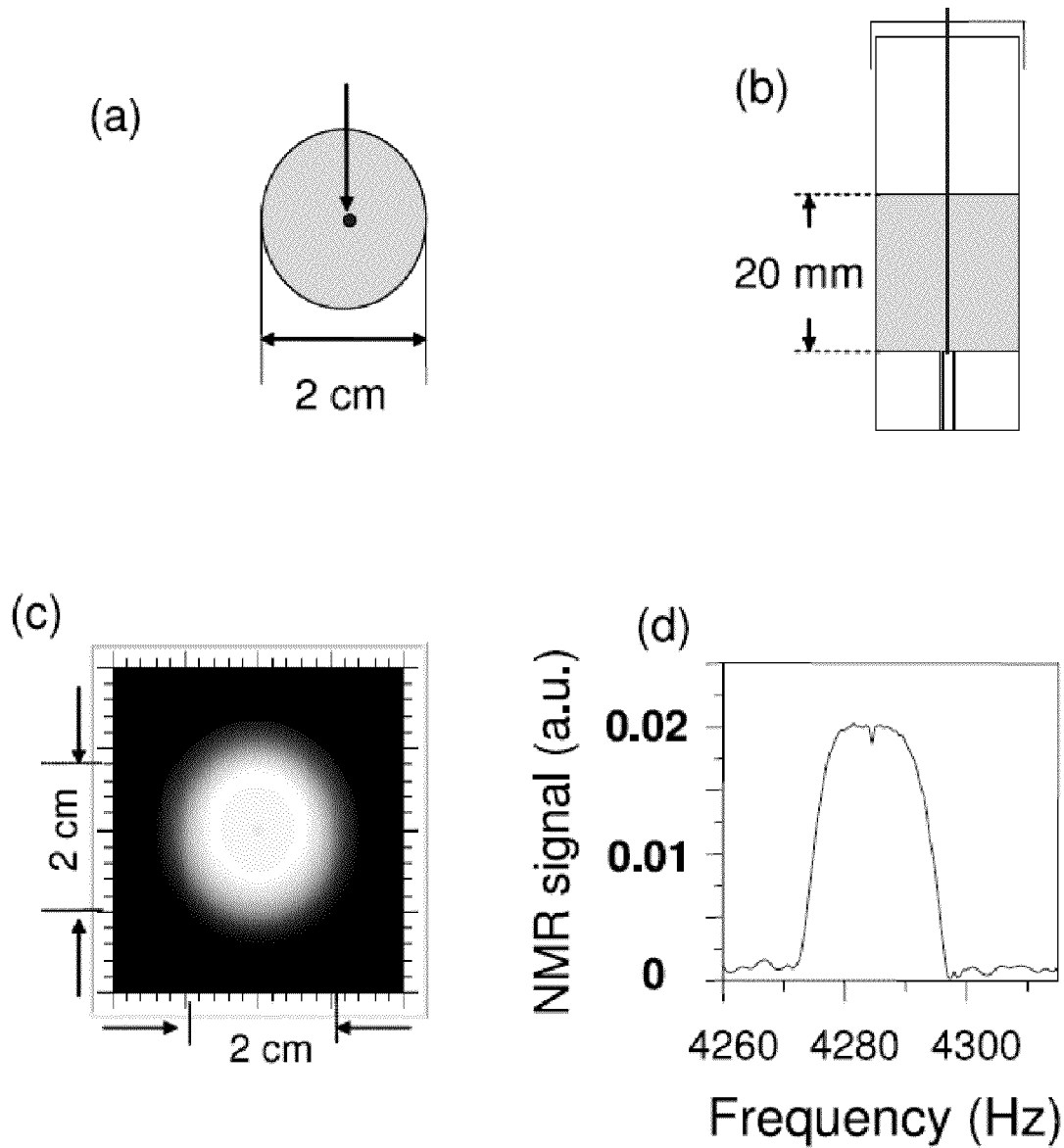
FIG. 16 shows (a) top view and (b) side view of a cylinder containing water with a capillary with magnetic fluid inserted into the center of the cylinder, with (c) the MRI image and (d) Fourier transform for the image shown in (c).

FIGS. 16(a) and (b) showed the top view and the side view of a cylinder containing 6.3 ml of water as well as a capillary filled with magnetic fluid (0.3 emu $g^{-1}$) placed at the axis of the cylinder. The capillary had an inner diameter of 0.25 mm and an outer diameter of 0.36 mm. FIGS. 16(c) and (d) showed the MRI image and its Fourier transform respectively. An image contrast was observed in the MRI image at the location of the capillary where it was filled with the magnetic fluid. The bright image showed an SNR of 20 while the central region showed an SNR of 16. The Fourier transform showed a dip at the resonating frequency and the 50% dip corresponds to a spatial resolution of about 1 mm.

Figure 17:
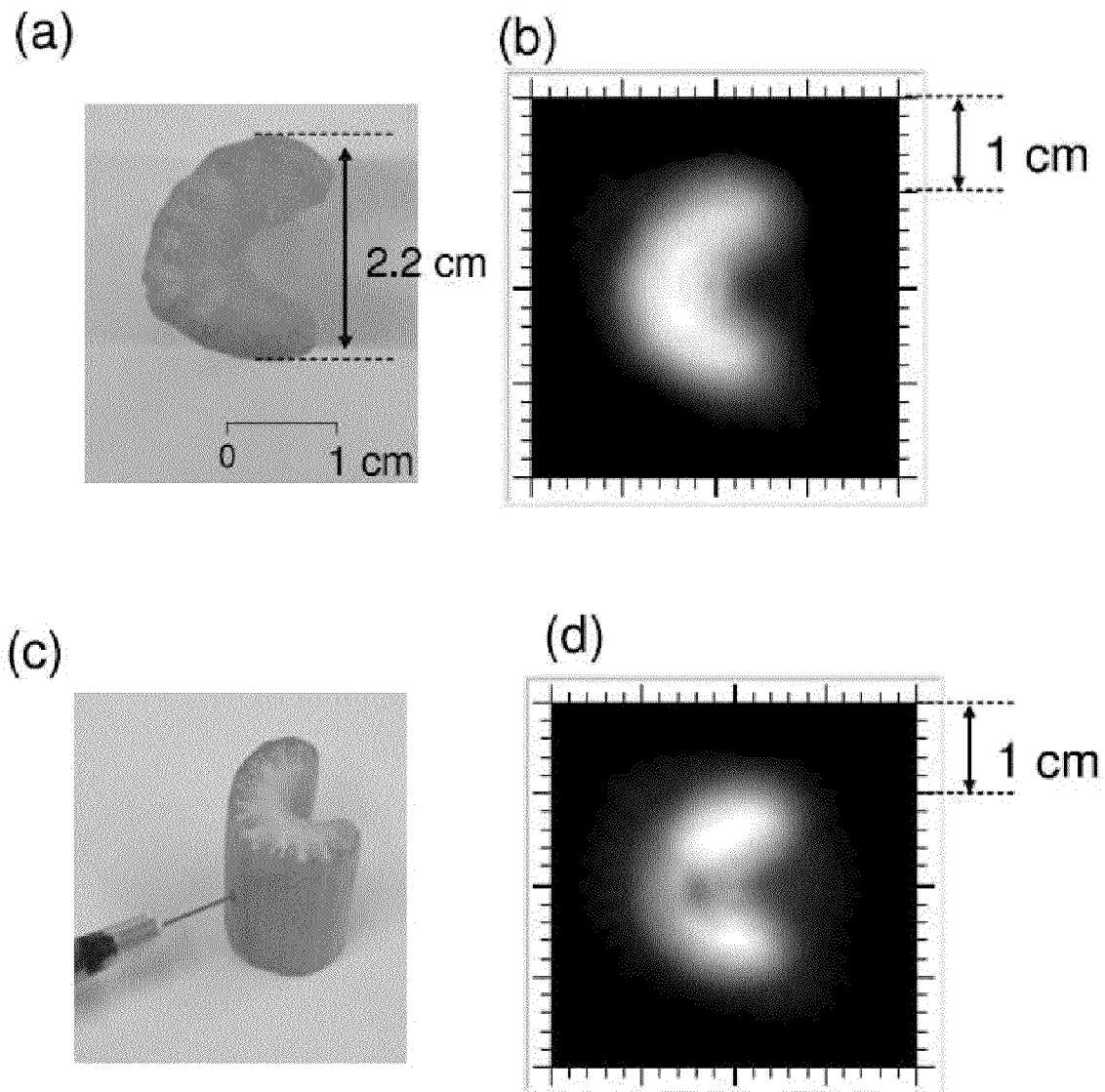
FIG. 17 shows (a) a photograph of a cut portion of celery, (b) magnetic resonance image of the portion of cut celery, (c) the cut portion of celery injected with magnetic fluid, and (d) the corresponding MRI image after injecting magnetic fluid.

FIGS. 17(a) and (b) were photographs showing a portion of cut celery and its corresponding MRI obtained after 50 averages, respectively. FIGS. 17(c) and (d) were photographs of a portion of celery injected with magnetic fluid and the corresponding MRI image after injecting 0.2 ml (0.3 emu $g^{-1}$) of magnetic fluids, respectively. Without the magnetic fluid it cannot be observed any image contrast. On the other hand, the image contrast was clearly enhanced at the location where magnetic fluid was injected. The MRI contrast in the central region was due to the effects of the magnetic susceptibility. The dephasing of the proton nuclear spin reduces the NMR intensity in that region.

What is claimed is:

1. An apparatus for detecting nuclear magnetic resonance (NMR) of a sample, comprising:
    (a) a pre-polarization coil for providing a millitesla magnetic field for prepolarizing nuclear spins in the sample;
    (b) a flux transformer for generating a magnetic flux signal of the sample consisting a pickup coil and an input coil, wherein the pickup coil is fitted into the pre-polarization coil; and
    (c) a high critical temperature ($T_c$) superconducting quantum interference device (SQUID) magnetometer for detecting nuclear magnetic resonance (NMR) signals from the sample, wherein the SQUID and the input coil are installed inside a superconducting vessel which shields environmental noise and sets the SQUID in a stable operation condition.

2. The apparatus of claim 1, wherein the detecting magnetic field is in the range of about 200 μT to about 1 μT and the prepolarizing magnetic field is in the range of about 10 mT or higher than 10 mT.

3. The apparatus of claim 1, wherein the superconducting vessel is composed of superconducting $Bi_2Sr_2Ca_2Cu_3O_y$.

4. The apparatus of claim 1, wherein the high-$T_c$ SQUID based NMR magnetoometer is set up in an electromagnetically shielded room.

5. The apparatus of claim 1, further comprising means to perform magnetic resonance imaging (MRI) of the sample by forming an image from the detected NMR signals.

6. The apparatus of claim 1, further comprising means for obtaining J-coupling information from the NMR signals.

* * * * *